US006093842A

United States Patent [19]
Oyevaar et al.

[11] Patent Number: 6,093,842
[45] Date of Patent: *Jul. 25, 2000

[54] PROCESS FOR CONTINUOUS PRODUCTION OF CARBONATE ESTERS

[75] Inventors: Martin H. Oyevaar, Goes, Netherlands; Bill W. To, Scarborough, Canada; Michael F. Doherty, Montague; Michael F. Malone, Amherst, both of Mass.

[73] Assignee: General Electric Company, Schenectady, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/160,661

[22] Filed: Sep. 25, 1998

[51] Int. Cl.$^7$ .................................................. C07C 68/06

[52] U.S. Cl. .......................................... 558/274; 558/271

[58] Field of Search ............................................. 558/274

[56] References Cited

U.S. PATENT DOCUMENTS

| | | |
|---|---|---|
| 2,829,153 | 3/1958 | Vodonik . |
| 3,914,290 | 10/1975 | Otsuki et al. . |
| 4,182,726 | 1/1980 | Illuminati et al. . |
| 4,192,949 | 3/1980 | Merger et al. . |
| 4,252,737 | 2/1981 | Krimm et al. . |
| 4,254,276 | 3/1981 | Iori et al. . |
| 4,410,464 | 10/1983 | Hallgren . |
| 4,552,704 | 11/1985 | Mark . |
| 4,554,110 | 11/1985 | Mark . |
| 4,609,501 | 9/1986 | Mark . |
| 5,034,557 | 7/1991 | Kiso et al. . |
| 5,149,856 | 9/1992 | Schon et al. . |
| 5,210,268 | 5/1993 | Fukuoka et al. . |
| 5,292,917 | 3/1994 | Nishihira et al. . |
| 5,334,742 | 8/1994 | Schon et al. . |
| 5,344,954 | 9/1994 | Schon et al. . |
| 5,354,923 | 10/1994 | Schon et al. . |
| 5,362,901 | 11/1994 | Wagner et al. . |

FOREIGN PATENT DOCUMENTS

| | | |
|---|---|---|
| 0 089 709 A1 | 9/1983 | European Pat. Off. . |
| 0 126 288 A2 | 11/1984 | European Pat. Off. . |
| 0 461 274 B1 | 6/1994 | European Pat. Off. . |
| 27 36 062 A1 | 8/1977 | Germany . |
| 38 08 427 A1 | 3/1988 | Germany . |
| 09300311 | 5/1994 | Italy . |
| 54 48732 | 4/1979 | Japan . |
| 61-291545 | 12/1986 | Japan . |
| 07304713 | 11/1995 | Japan . |
| 7330687 | 12/1995 | Japan . |

OTHER PUBLICATIONS

English Translation of Process Description submitted by Enichem to Ravenna, Italy (Aug. 5, 1996).

Consider Reactive Distillation, J.L. DeGarmo, V.N. Parulekar, and Pinjala, Koch Engineering Company, Chemical Engineering Progress, Mar. 1992, pp. 43–51.

Reactions in Distillatin Columns, Gerd Kaibel, Hans–Horst Mayer & Bernhard Seid, Chem. Ing–Tech. 50 (1978) No. 8.pp. 586–592.

Process Engineering Methods for Continuous Reactions Involving Superposed Distillation, Ulrich Block, Chem. Ing. Tech. [Chemical Engineering Technology] 49 (1977), No. 2, p. 151.

Multistage Distillation With Chemical Reaction, P. Baratella, S. Carra, G. Giardini, R.S. Santi, ING. CHIM. ITAL., v. 10, n. 1, gennaio 1974, pp. 1–6.

Simulation of Continuous Reactive Distillation By A Homotopy–Continuation Method, Y.A. Chang and J.D. Seader, Received Mar. 25, 1988; final revision received May 5, 1988; received for publication May 19, 1988.

Distillation With Chemical Reaction, Paul Donald Babcock, Dissertation, Lehigh University, 1974.

Selection of Reactors for Reactions With Superposed Distillation, Hans–Horst Mayer and Otto Worz, Gen. Chem. Eng. 3 (1980) pp. 252–257.

Chemical Reaction and Reactor Engineering, James J. Carberry and Arvind Varma, Department of Engineering, Univeristy of Notre Dame, Notre Dame, IN.

Reactive Distillation: Technology and Its Applications, D. Cieutat, Lummus Crest Inc., Pétrole et Techniques, No. 350, Sep.–Oct. 1989, pp. 36–40.

Reactive Distillation: Principle, Applications and Prospects, Paul Mikitenko, Institut Français du Pétrole, Pétrole et Techniques, No. 329, Dec. 1986, pp. 34–38.

Catalytic Distillation Combining Chemical Reaction With Product Separation, William P. Stadig, Feb. 1987 Chemical Processing.

Encyclopedia of Chemical Processing and Design, Crystallization, Nucleation Systems to Design Data—Importance of Accuracy, John J. McKetta, William A. Cunningham, vol. 14, 1982.

(List continued on next page.)

Primary Examiner—Michael G. Ambrose

[57] ABSTRACT

Production of diaryl carbonate esters by reaction of a dialkyl carbonate and an aromatic alcohol to form a diaryl carbonate and an alkyl alcohol is accomplished by introducing three reactant streams into an extractive/reactive distillation column in the presence of a transesterification catalyst. The three reactant streams are a first reactant stream containing a dialkyl carbonate, a second reactant stream containing an aromatic alcohol, and a third reactant stream containing an entraining agent. The entraining agent is selected from among compounds that do not form azeotropes with the dialkyl carbonate or the alkyl alcohol and that boil at a higher temperature than either the dialkyl carbonate or the alkyl alcohol. The first reactant stream is introduced into the column below the second reactant stream, and the second reactant stream is introduced into the column below the third reactant stream. A product stream containing diaryl carbonate esters is recovered from the bottom of the column.

39 Claims, 1 Drawing Sheet

OTHER PUBLICATIONS

Continuous–Flow Processes Under Gas–Liquid Phase––Transfer Catalysis (GL–PTC) Conditions: The Reaction of Dialkyl Carbonates With Phenols, Alcohols, and Mercaptans; Kinetics and Catalysis, Pietro Tundo, Francesco Trotta, Giovanni Moraglio, Ferdinando Ligorati, Ind. Eng. Chem. Res., vol. 27, No. 9, 1988, pp. 1565–1571.

Synthesis of Anisole by Lewis acid Catalysed Decarboxylation of Methyl Phenyl Carbonate, Pierre Braunstein, Mohammed Lakkis, Dominique Matt, Serge Lécolier, Journal of Molecular Catalysis, 42 (1987) pp. 353–355.

Partial English Translation of Kagaku–Kogaku Yogo–Jiten, (Dictionary of Chemical Engineering Terms), edited by T. Shirozuka et al., published by Ohm Publishing Co., Ltd., Japan, 1967, p. 27.

Dimethyl Carbonate: A New Building Block for Organic Chemicals Production, Marcello Massi Mauri, Ugo Romano, Franco Rivetti, Paper presented at VI National Meeting of Italian Chemical Society, Industrial Chemistry Division, Torino, Sep. 20–23, 1983.

PROCESS FOR CONTINUOUS PRODUCTION OF CARBONATE ESTERS

FIELD OF THE INVENTION

This application relates to a process for continuous production of carbonate esters, particularly aromatic carbonate esters.

Production of aromatic carbonate esters can be accomplished by reaction of aromatic alcohols with phosgene. However, the toxicity of phosgene has led many to prefer the use of a catalytic transesterification reaction in which a dialkyl carbonate is reacted with an aromatic alcohol in the presence of a suitable catalyst to produce arylalkylcarbonates and diaryl carbonates. This reaction is generally slow, however, and has an unfavorable equilibrium point which makes recovery of substantial yields of product challenging. Further, the reaction produces an alkyl alcohol co-product which can form an azeotrope with the dialkyl carbonate reactant. This means that one cannot simply distill off the co-product to shift the equilibrium in favor of the desired aromatic carbonates, because dialkyl carbonate reactant is lost in the process as well. Moreover, recovered azeotrope must be separated to allow recycling of the unused reactant.

Two basic approaches have been considered, separately or in combination, to minimize these problems with catalytic transesterification processes for the production of aromatic carbonates. The first approach is the development of improved catalysts, as reflected in U.S. Pat. Nos. 4,182,726, 4,554,110, 4,552,704, and 4,609,501 which are incorporated herein by reference. Such catalysts may improve the reaction rate, but they fail to address the limitations imposed on the process by the unfavorable equilibrium and azeotrope formation.

A second approach attempts to bias the equilibrium of the carbonate forming reaction towards the products. For example, JP 54-48732 discloses the addition of an azeotrope-forming agent (heptane), to the reaction mixture to facilitate removal of the alkyl alcohol. U.S. Pat. No. 4,410,464, incorporated herein by reference, discloses absorbing the alkyl alcohol into molecular sieves. The difficulty with both of these approaches is that there are additional steps involved to recover the co-products from the azeotrope or the molecular sieve. These additional steps lead to higher operating and capital costs which are economically undesirable when operating on a commercial scale.

Various attempts have also been made to combine distillation and reaction columns. For example, European Patent Pub. 0 461 274 discloses a method for producing diaryl carbonates in one or more continuous multistage distillation columns. The initial column is supplied with a reactant stream containing all of the reactants and catalyst, and a mixture of products is continuously withdrawn from the bottom of the column. Additional dimethylcarbonate can be added as a gas near the bottom of the column. This method still does not avoid loss of dialkyl carbonate reactant with the top product of the initial column due to the formation of an azeotrope.

There remains a need for an economical method for production of aromatic carbonates on a commercial scale, and in particular for a method for production of aromatic carbonates which efficiently utilizes the starting materials without formation of an azeotrope by-product. It is an object of the present invention to provide such a method.

SUMMARY OF THE INVENTION

The present invention provides a method for production of diaryl carbonate esters by reaction of a dialkyl carbonate and an aromatic alcohol to form a diaryl carbonate and an alkyl alcohol. In accordance with the invention, three reactant streams are introduced into an extractive/reactive distillation column in the presence of a transesterification catalyst. The three reactant streams are a first reactant stream comprising a dialkyl carbonate, a second reactant stream comprising an aromatic alcohol, and a third reactant stream comprising an entraining agent. The entraining agent is selected from among compounds that do not form azeotropes with the dialkyl carbonate or the alkyl alcohol and that boil at a higher temperature than either the dialkyl carbonate or the alkyl alcohol.

In the method of the invention, the first reactant stream is introduced into the column below the second reactant stream, and the second reactant stream is introduced into the column below the third reactant stream. A product stream containing diaryl carbonate esters is recovered from the bottom of the column.

DETAILED DESCRIPTION OF THE INVENTION

Figure 1:
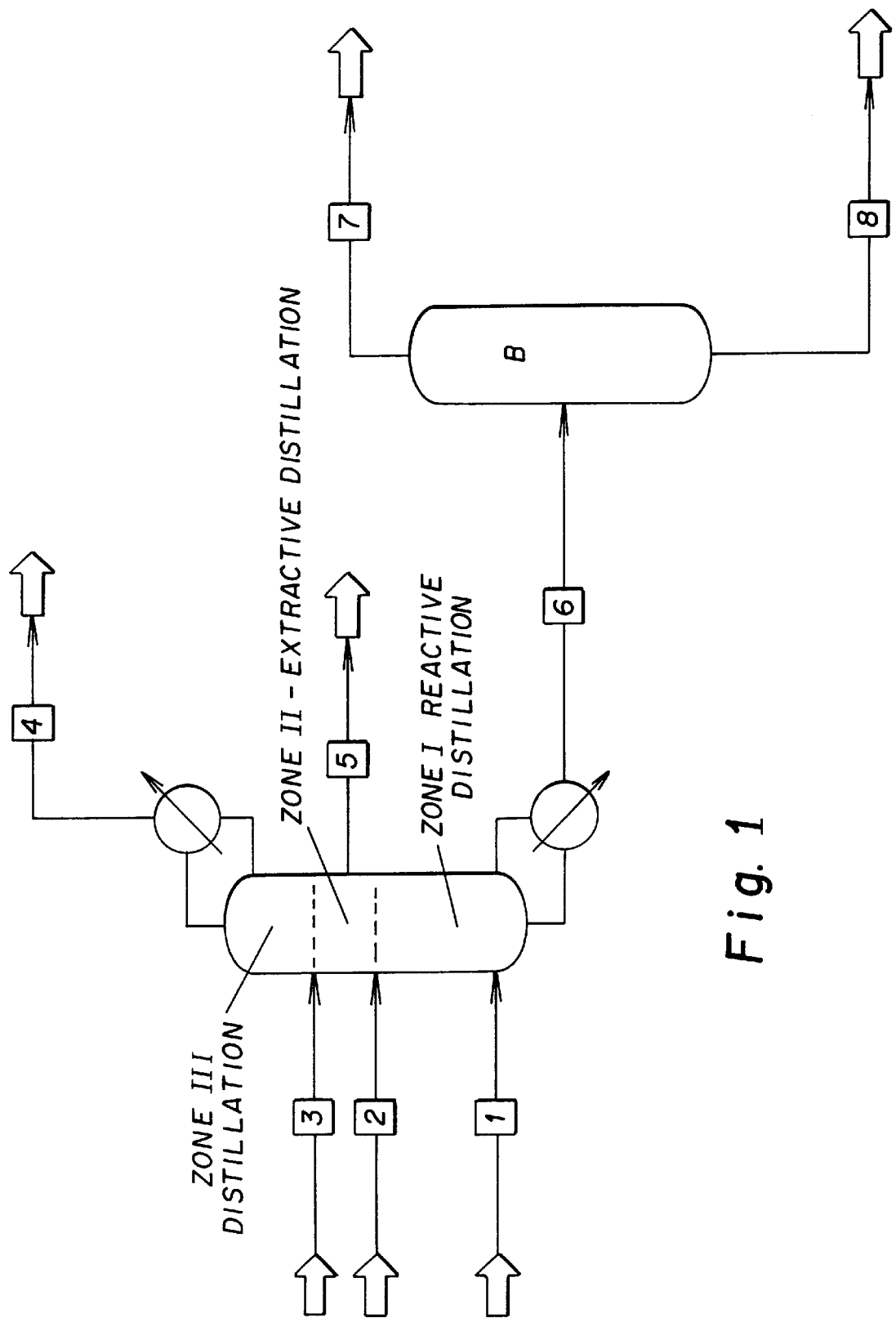
FIG. 1 is a schematic illustration of an apparatus suitable for performing the method of the present invention.

The present invention provides a method for production of diaryl carbonate esters by reaction of a dialkyl carbonate and an aromatic alcohol to form a diaryl carbonate and an alkyl alcohol without the production of azeotropic mixtures. The overall process involves a two-step reaction as follows:

dialkyl carbonate+aromatic alcohol→arylalkyl carbonate+alkyl alcohol    (1)

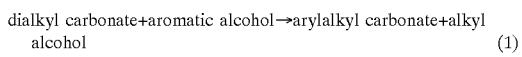

2 arylalkyl carbonate→dialkyl carbonate+diaryl carbonate    (2).

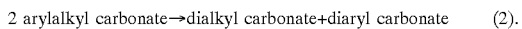

While the dialkyl carbonate used as a starting material in the method of the invention may in theory be any dialkyl carbonate, it will be appreciated that in practice it will be preferred to use a dialkyl carbonate with a small alkyl group, such as, for example, dimethyl carbonate. Dimethyl carbonate is readily and economically available. Further, the resulting alkyl alcohol (methanol) has a low boiling point relative to other alkyl alcohols so that it can be separated from the other components of the reaction mixture by distillation with minimum expenditure of energy.

The aromatic alcohol used as a starting material in the method of the invention is selected to provide the desired product. Examples of aromatic alcohols useful in the invention include but are not limited to those disclosed in EP 0 461 274, namely those represented by formula ArOH, wherein Ar represents an aromatic group having 5 to 30 carbon atoms. Examples of specific ArOH compounds include but are not limited to phenol; various alkyl phenols, such as cresol, xylenol, trimethylphenol, tetramethylphenol, ethylphenol, propylphenol, butylphenol, diethylphenol, methylethylphenol, methylpropylphenol, dipropylphenol, methylbutylphenol, pentylphenol, hexylphenol and cyclohexylphenol; various alkoxyphenols, such as methoxyphenol and ethoxyphenol; various substituted phenols represented by the formula:

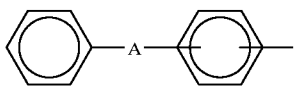

wherein A represents a bond, a divalent group, such as —O—, —S—, —CO— and —SO$_2$—, an alkylene group, a substituted alkylene group of the formula:

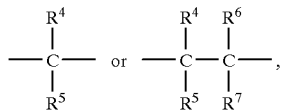

wherein each of $R_4$, $R_5$, $R_6$ and $R_7$ individually represents a hydrogen atom, a lower alkyl group, a cycloalkyl group, an aryl group or an aralkyl group, which may be substituted with a halogen atom or an alkoxy group), or a cycloalkylene group of the formula:

wherein k is an integer of from 3 to 11, and the hydrogen atoms may be substituted with a lower alkyl group, an aryl group, a halogen atom or the like, and the aromatic group may be substituted with a substituent, such as a lower alkyl group, a lower alkoxy group, an ester group, a hydroxyl group, a nitro group, a halogen and a cyano group; naphthol and various substituted naphthols; and heteroaromatic hydroxy compounds, such as hydroxypyridine, hydroxycumarine and hydroxyquinoline. Also usable are aromatic dihydroxy compounds having two hydroxyl groups, such as hydroquinone, resorcinol, catechol, dihydroxynaphthalene, dihydroxyanthracene dihydroxy compounds obtained by substitution of the above with an alkyl group; and aromatic dihydroxy compounds represented by the formula:

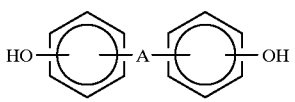

wherein A is as defined above, and the aromatic ring may be substituted with a substituent, such as a lower alkyl group, a lower alkoxy group, an ester group, a nitro group, a cyano group and a halogen atom.

The dialkyl carbonate and the aromatic alcohol are introduced separately as part of separate reactant streams into an extractive/reactive distillation column in the presence of a transesterification catalyst. Many transesterification catalysts capable of catalyzing the reactions described above are known. Examples of suitable transesterification catalysts include but are not limited to those disclosed in EP 0 461 274, namely lead compounds, particularly lead oxides such as PbO, PbO$_2$ and Pb$_3$O$_4$; lead sulfides, such as PbS and Pb$_2$S; lead hydroxides, such as Pb(OH)$_2$ and Pb$_2$O$_2$(OH)$_2$; plumbites, such as Na$_2$PbO$_2$, K$_2$PbO$_2$, NaHPbO$_2$ and KHPbO$_2$; plumbates, such as Na$_2$PbO$_3$, Na$_2$H$_2$PbO$_4$, K$_2$PbO$_3$, K$_2$(Pb(OH)$_6$), K$_4$PbO$_4$, Ca$_2$PbO$_4$ and CaPbO$_3$; lead carbonates and basic salts thereof, such as PbCO$_3$ and 2PbCO$_3$ Pb(OH)$_2$; lead salts of organic acids, and carbonates and basic salts thereof, such as Pb(OCOCH$_3$)$_2$, Pb(OCOCH$_3$)$_4$ and Pb(OCOCH$_3$)$_2$ PbO.3H$_2$O; organolead compounds, such as Bu$_4$Pb, Ph$_4$Pb, Bu$_3$PbCl, Ph$_3$PbBr, Ph$_3$Pb (or Ph$_6$Pb$_2$), Bu$_3$PbOH and Ph$_3$PbO wherein Bu represents a butyl group and Ph represents a phenyl group; alkoxylead compounds and aryloxylead compounds, such as Pb(OCH$_3$)$_2$, (CH$_3$O)Pb(OPh) and Pb(OPh)$_2$; lead alloys, such as Pb—Na, Pb—Ca, Pb—Ba, Pb—Sn and Pb—Sb; lead minerals, such as galena and zincblende; and hydrates of these lead compounds; compounds of copper family metals (copper, silver and gold), particularly, salts or complexes of copper family metals, such as CuCl, CuCl$_2$), CuBr, CuBr$_2$, CuI, CuI$_2$, Cu(OAc)$_2$, Cu(acac)$_2$, copper oleate, Bu$_2$Cu, (CH$_3$)O)$_2$)Cu, AgNO$_3$), AgBr, silver picrate, AgC$_6$H$_6$ClO$_4$, Ag(bullvalene)$_3$NO$_3$, (AuC°C—C(CH$_3$)$_3$)$_n$ and (Cu(C$_7$H$_8$)Cl)$_4$ wherein OAc represents an acetyl group and acac represents an acetylacetone chelate ligand; alkali metal complexes, such as Li(acac) and LiN(C$_4$H$_9$)$_2$) wherein acac is as defined above; zinc complexes, such as Zn(acac)$_2$; cadmium complexes, such as Cd(acac)2, compounds of iron family metals such as Fe(C$_{10}$H$_8$)(CO)$_5$, Fe(CO)$_5$, Fe(C$_3$H$_6$)(CO)$_3$, Co(mesitylene)$_2$(PEt$_2$Ph)$_2$, CoC$_5$F$_5$(CO)$_2$, Ni—(p)—C$_5$H$_5$NO and ferrocene; zirconium complexes, such as Zr(acac)4 and zirconocene; Lewis acids and Lewis acid-forming transition metal compounds, such as AlX$_3$, TiX$_3$, TiX$_4$, VOX$_3$, VX$_5$, ZnX$_2$, FeX$_3$, and SnX$_4$ wherein X represents a halogen, an acetoxy group, an alkoxy group or an aryloxy group; organotin compounds, such as (CH$_3$)$_3$SnOCOCH$_3$, (C$_2$H$_5$)$_3$SnOCOC$_6$H$_5$, Bu$_3$SnOCOCH$_3$, Ph$_3$SnOCOCH$_3$, Bu$_2$Sn(OCOCH$_3$)$_2$, Bu$_2$Sn(OCOC$_{11}$H$_{23}$)$_2$, Ph$_3$SnOCH$_3$, (C$_2$H$_5$)$_3$SnOPh, Bu$_2$Sn(OCH$_3$)$_2$, Bu$_2$Sn(OC$_2$H$_5$)$_2$, Bu$_2$Sn(OPh)$_2$, Ph$_2$Sn(OCH$_3$)$_2$, (C$_2$H$_5$)$_3$SnOH, Ph$_3$SnOH, Bu$_2$SnO, (C$_8$H$_{17}$)$_2$SnO, Bu$_2$SnCl$_2$ and BuSnO(OH); inorganic oxides, such as silica, alumina, titania, silicatitania, zinc oxide, zirconium oxide, gallium oxide zeolite and oxides of a rare earth; and a material obtained by modifying the surface acid site of the above inorganic oxide by silylation or other methods.

The catalyst is preferably provided as part of one of the reactant streams. However, the catalyst might also be provided as a separate (fourth) reactant stream, or be provided in an immobilized form within the column.

FIG. 1 shows a schematic illustration of system for making diaryl carbonates that includes an extractive/reactive distillation column A. An extractive/reactive column does not have to have any particular packing or other internal structure. In general, like any distillation column, internals should be used that promote good mixing/contact between gas and liquid going up and down through the column. Some catalysts may be particularly compatible with certain special designs which promote gas-liquid-solid catalyst contacting. For example, one may find that certain of the catalyst systems mentioned above give better performance when used in a catalytic packing system such as those discussed by J. L. DeGarmo, V. N. Parulekar and V. Pinjala of Koch Engineering Company in their article *Consider Reactive Distillation*, Chemical Engineering Progress, March 1992, pp. 42–51. Three streams are fed into the extractive/reactive distillation column A. Stream 1 contains the alkyl carbonate reactant. Stream 2 contains the aromatic alcohol reactant, and preferably also the catalyst. Stream 3 contains an entraining agent.

The entraining agent is a compound that does not form azeotropes with the dialkyl carbonate or the alkyl alcohol and that boils at a higher temperature than either the dialkyl carbonate or the alkyl alcohol. Depending on the properties of the aromatic alcohol employed, the entraining agent may be identical to the aromatic alcohol. For example, phenol may be used as both the aromatic alcohol and the entraining agent for the efficient production of diphenyl carbonate. The ability to utilize the same material as both the aromatic alcohol and the entraining agent offers several benefits. First, there is a reduction in the introduction of impurities since only one material is being used. Second, processing costs are reduced since there is no need for a separate system to separate and recover the entraining agent.

If the aromatic alcohol employed tends to form azeotropes or has an unsuitable boiling point, then other materials such as anisole can be used as the entraining agent. Anisole and similar materials may also be used in combination with aromatic alcohols to make up the entraining agent.

Streams 1, 2 and 3 are fed continuously into extractive/reactive distillation column A in FIG. 1. Mass ratios of stream 1 and 2 can be varied to maximize production of the desired product. As this is in large part dependent of column conditions, the preferred mass ratios are appropriately determined empirically for a given reaction and column. In general, however, the mass ratio of stream 1 to stream 2 will vary between about 10:1 and 1:10, preferably from about 1:1 to 1:5. The mass ratios of streams 1 and 3 can be varied to change the purity of the overhead product (stream 4) and to change the temperature and composition in stream 6. The mass ratio of stream 1 to stream 3 may vary between 1:20 and 20:1, preferably from about 1:5 to 1:10.

The column A is maintained at pressures and temperatures suitable for the production of aromatic carbonates. While these conditions will depend on the precise combination of reactants and catalyst employed and the column configuration, geometry and internal structure, temperatures of from 190 to 260° C. and pressures of from 1 to 10 bars will generally be suitable.

Under these conditions, three distinct zones can be identified within column A. In Zone I, as shown in FIG. 1, reactive distillation occurs, whereby reactions (1) and (2) take place to produce aromatic carbonates. The products of the reaction are recovered as a liquid stream 6 from near the bottom of the column. In Zone II, extractive distillation occurs which prevents formation of an azeotropic mixture. In Zone III, distillation occurs to produce stream 4 which contains the alkyl alcohol (generally about 95% by weight) and other light gases such as $CO_2$, nearly free of alkyl carbonate (i.e., less than 1% by weight). This stream may be condensed for recycling, for example in the production of alkyl carbonates for use as the starting material in the method of the invention.

An additional stream 5 may optionally be included to withdraw by-products from the center of the column which may negatively affect the reaction.

In a preferred embodiment, substantially pure dimethylcarbonate is fed as Stream 1 into the bottom of the column. Stream 2 consists of 50–99 weight % phenol with the balance being catalyst, optionally combined with a recycled stream recovered from downstream in the process, for example containing e.g., anisole, dimethyl carbonate, methanol, benzoates and heavy materials. Stream 3 is a substantially pure phenol as the entraining agent. In this case, product Stream 6 will typically contain 5 to 20 weight % diphenyl carbonate, 5 to 25 weight % methylphenyl carbonate, 2 to 15% unreacted dimethylcarbonate, 50 to 90% phenol entraining agent/reactant and a balance of reaction by-products. Catalyst is also recovered in Stream 6 and through an optional side-draw near the bottom of the column.

Product stream 6 can be further processed to continue the reaction and purify the product stream in one or more additional columns represented by Unit B in FIG. 1. Unit B is suitably a reactive distillation column which may have differing configuration geometry, internal structure and operating conditions.

We claim:

1. A method for production of diaryl carbonate esters by reaction of a dialkyl carbonate and an aromatic alcohol to form a diaryl carbonate and an alkyl alcohol, comprising the steps of
    (a) introducing three reactant streams into an extractive/reactive distillation column in the presence of a transesterification catalyst,
    wherein the three reactant streams are
        a first reactant stream comprising a dialkyl carbonate,
        a second reactant stream comprising an aromatic alcohol, and
        a third reactant stream comprising an entraining agent, said entraining agent being selected from among compounds that do not form azeotropes with the dialkyl carbonate or the alkyl alcohol and that boil at a higher temperature than either the dialkyl carbonate or the alkyl alcohol, and
    wherein said first reactant stream is introduced into the column below the second reactant stream, and said second reactant stream is introduced into the column below the third reactant stream; and
    (b) recovering a product stream containing diaryl carbonate esters from the extractive/reactive distillation column.

2. The method of claim 1, wherein the catalyst is introduced into the column as part of the second reactant stream.

3. The method according to claim 2, wherein the entraining agent and the aromatic alcohol are the same compound.

4. The method according to claim 3, wherein the entraining agent and the aromatic alcohol are phenol.

5. The method according to claim 1, wherein the dialkyl carbonate is dimethylcarbonate.

6. The method of claim 5, wherein the catalyst is introduced into the column as part of the second reactant stream.

7. The method according to claim 6, wherein the entraining agent and the aromatic alcohol are the same compound.

8. The method according to claim 7, wherein the entraining agent and the aromatic alcohol are phenol.

9. The method according to claim 1, further comprising the step of processing the product stream recovered from the extractive/reactive distillation column by processing in a second column.

10. The method according to claim 9, wherein the second column is a reactive distillation column.

11. The method according to claim 1, wherein the extractive/reactive distillation column is maintained at a temperature of from 190 to 260° C. and a pressure of from 1 to 10 bars.

12. The method of claim 11, wherein the catalyst is introduced into the column as part of the second reactant stream.

13. The method according to claim 12, wherein the entraining agent and the aromatic alcohol are the same compound.

14. The method according to claim 13, wherein the entraining agent and the aromatic alcohol are phenol.

15. The method according to claim 11, wherein the dialkyl carbonate is dimethylcarbonate.

16. The method of claim 15, wherein the catalyst is introduced into the column as part of the second reactant stream.

17. The method according to claim 16, wherein the entraining agent and the aromatic alcohol are the same compound.

18. The method according to claim 17, wherein the entraining agent and the aromatic alcohol are phenol.

19. The method according to claim 11, further comprising the step of processing the product stream recovered from the extractive/reactive distillation column by processing in a second column.

20. The method according to claim 19, wherein the second column is a reactive distillation column.

21. The method according to claim 11, wherein the mass ratio of the first reactant stream to the second reactant stream is from 10:1 to 1:10.

22. The method according to claim 21, wherein the mass ratio is from 1:1 to 1:5.

23. The method according to claim 1, wherein the mass ratio of the first reactant stream to the second reactant stream is from 10:1 to 1:10.

24. The method according to claim 23, wherein the mass ratio is from 1:1 to 1:5.

25. The method according to claim 11, wherein the mass ratio of the first reactant stream to the third reactant stream will vary between 1:20 and 20:1.

26. The method according the claim 25, wherein the mass ratio of the first reactant stream to the third reactant stream will vary between 1:5 to 1:10.

27. The method according the claim 1, wherein the mass ratio of the first reactant stream to the third reactant stream will vary between 1:20 and 20:1.

28. The method according to claim 27, wherein the mass ratio of the first reactant stream to the third reactant stream will vary between 1:5 and 1:10.

29. The method of claim 23, wherein the catalyst is introduced into the column as part of the second reactant stream.

30. The method according to claim 23, wherein the entraining agent and the aromatic alcohol are the same compound.

31. The method according to claim 30, wherein the entraining agent and the aromatic alcohol are phenol.

32. The method according to claim 23, wherein the dialkyl carbonate is dimethylcarbonate.

33. The method of claim 32, wherein the catalyst is introduced into the column as part of the second reactant stream.

34. The method according to claim 33, wherein the entraining agent and the aromatic alcohol are the same compound.

35. The method according to claim 34, wherein the entraining agent and the aromatic alcohol are phenol.

36. The method according to claim 23, further comprising the step of processing the product stream recovered from the extractive/reactive distillation column by processing in a second column.

37. The method according to claim 36, wherein the second column is a reactive distillation column.

38. The method according to claim 1, wherein the entraining agent and the aromatic alcohol are the same compound.

39. The method according to claim 1, wherein further comprising the step of recovering alkyl alcohol as a second product stream.

* * * * *